United States Patent [19]

Perser et al.

[11] Patent Number: 4,459,980
[45] Date of Patent: Jul. 17, 1984

[54] ANKLE AND FOOT BRACE

[75] Inventors: Donald A. Perser, Northbrook; Erich W. Mohn, Morton Grove, both of Ill.

[73] Assignee: Ballert Orthopedic Corporation, Northbrook, Ill.

[21] Appl. No.: 389,690

[22] Filed: Jun. 18, 1982

[51] Int. Cl.³ .............................................. A61F 3/00
[52] U.S. Cl. .......................... 128/80 E; 128/DIG. 15
[58] Field of Search ................ 128/80 E, 80 H, 87 R, 128/165, 166, DIG. 15

[56] References Cited

U.S. PATENT DOCUMENTS

| | | | |
|---|---|---|---|
| 2,439,100 | 4/1948 | Richards | 128/80 E |
| 2,440,894 | 5/1948 | Caesar | 128/80 E |
| 2,712,310 | 7/1955 | Giambra | 128/80 E |
| 3,454,002 | 7/1969 | Westlake et al. | 128/87 R |
| 3,859,991 | 1/1975 | Theodores | 128/80 E |

FOREIGN PATENT DOCUMENTS

| | | | |
|---|---|---|---|
| 117877 | 8/1918 | United Kingdom | 128/80 E |
| 701746 | 12/1953 | United Kingdom | 128/80 E |

Primary Examiner—John D. Yasko
Attorney, Agent, or Firm—Ronald A. Sandler

[57] ABSTRACT

The invention disclosed herein is an ankle and foot brace adjustable readily to fit numerous sizes of shoes and legs, the brace includes a pair of spaced leg members, each leg member having means for adjusting the length of the leg member; an adjustable calf attachment means is cooperatively carried by each of the leg members adjacent to the upper ends thereof and extends in use about the wearer's calf for respectively securing the leg members thereto; a bias means on the other end of each leg member to provide dorsiflexion assistance to the wearer's shoes by an adjustable clamping means carried by the leg members adjacent to the lower ends thereof and attaching in use about the wearer's shoe for securing the leg member thereto.

3 Claims, 4 Drawing Figures

ANKLE AND FOOT BRACE

FIELD OF THE INVENTION

This invention relates generally to human leg braces and more particularly to an ankle and foot brace which provides dorsiflexion assistance to the foot of the wearer.

BACKGROUND OF THE INVENTION

Where a patient's leg has been weakened by disease such as a stroke, treatment often requires supporting the leg or foot with a suitable brace which will allow the patient to walk naturally. U.S. Pat. No. 3,805,773, assigned to applicants' assignee, discloses a fully adjustable training assist brace frequently used as an aid in evaluating physical therapy treatment.

After evaluation by a medical professional, it is sometimes detemined that a brace is required to provide ankle and foot motion that the patient has lost. Often, the patient's ankle and foot only needs assistance in returning to the standing upright position while walking. It is a primary object of the invention to fulfill this need and provide a brace capable of being readily applied or removed from a patient's shoe and leg so that the brace fits with maximum comfort, yet may be used on numerous patients, with varying size legs and feet.

SUMMARY OF THE INVENTION

The present invention comprises a novel ankle and foot brace capable of providing dorsiflexion assistance to the foot of the wearer. Use of the novel brace is especially warranted in those instances where a patient requires dorsiflexion assistance and can wear the brace for everyday use.

It is a primary object of the invention to provide an ankle and foot brace of the type set forth which may be adjustable circumferentially to accommodate the calf portion of the patient's leg, and featuring anterior and posterior openings to accommodate an easy fit with the convenience and simplicity of using a fastening means like Velcro patches.

A further object of the present invention is to provide an ankle and foot brace which includes adjustable leg members to adapt longitudinally to the size of the patient's leg.

It is another object to the present invention to provide an ankle and foot brace adjustable readily to fit either the right or left foot of the patient and adjustable to various shoe sizes.

It is yet another object of the present invention to provide an ankle and foot brace which may use various types of shoes with a normal heel to maximize patient comfort.

It is still another object of the present invention to provide an ankle and foot brace providing a simple design, easy to manufacture and use with shoes, with a normal heel, making the present invention inexpensive for the patient to appropriate.

It is another object of the present invention to provide an ankle and foot brace which does not require damaging the shoe in order to attach it.

Disclosed herein is an ankle and foot brace adjustable readily to fit numerous sizes of shoes and legs. The brace includes a pair of spaced leg members, each leg member having means for adjusting the length of the leg member. An adjustable calf attachment means is cooperatively carried by each of the leg members adjacent to the upper ends thereof and extends in use about the wearer's calf for respectively securing the leg members thereto. The brace also includes a bias means on the other end of each leg member to provide dorsiflexion assistance to the wearer's shoes by an adjustable clamping means carried by the leg members adjacent to the lower ends thereof and attaching in use about the wearer's shoe for securing the leg member thereto.

To the accomplishment of the foregoing and still other objects and advantages, the invention is best utilized in an ankle and foot brace adjustable readily to fit numerous sizes of shoes and legs. The brace includes a pair of spaced leg members having a general rod-like configuration, each leg member having a first portion of rod-like configuration and a second portion of sleeve-like configuration to form an overlapping relationship. The first portion moves within the second portion to adjust the length of the leg members. A pair of calf bands respectively connects to opposite sides of the leg members and cooperates to surround the wearer's calf with the free ends of one of the calf bands respectively disposed in overlapping relationship with the free ends of the other calf band, and fastening means for securing together the overlapping ends of the calf bands. The brace also includes a spring having a coil-like configuration being integrally formed with each leg member and aligned to provide dorsiflexion assistance to the wearer's shoe. An adjustable clamp having a pair of jaws and adjusting screw is included in the brace. Each jaw has a slot for receiving the sole of the wearer's shoe. The first jaw has a bore for holding the head of the screw and the second has a threaded bore for receiving the threaded portion of the screw. The screw traverses the shoe's sole and parallels the underside of the sole. Each jaw has a second bore in parallel alignment to the slot for receiving the leg members and for abutting the lower ends of the leg members against the heel of the wearer's shoe. The lower ends extend through the second bore rearward of the jaw and toward the heel of the shoe, each jaw has a first abutment surface for engaging the edge of the sole, and a second abutment surface for engaging the underside of the sole.

BRIEF DESCRIPTION OF THE DRAWINGS

The invention, both as to its organization and method of operation, together with further objects and advantages thereof, would best be understood by reference to the following specification taken in connection with the accompanying drawings, in which.

DETAILED DESCRIPTION OF THE DRAWINGS

Figure 1:
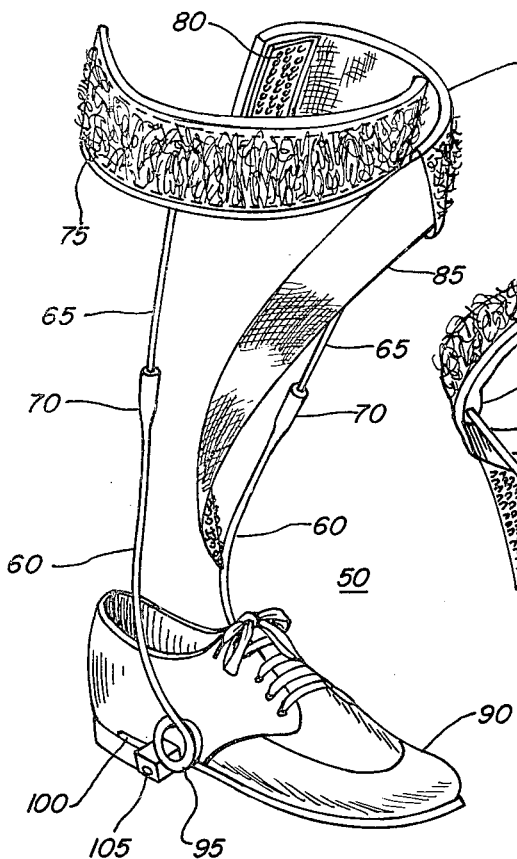
FIG. 1 is a front perspective view of an ankle and foot brace constructed in accordance with and embodying the features of the present invention.
Figure 2:
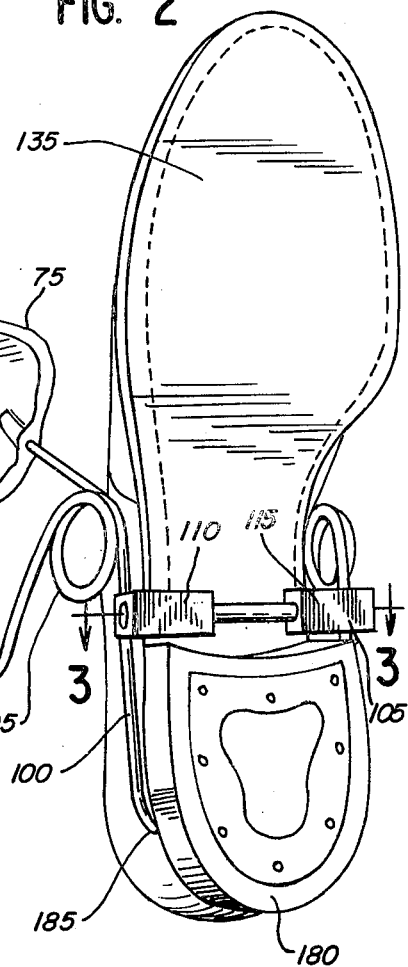
FIG. 2 is a bottom perspective view of the ankle and foot brace of FIG. 1, showing an adjustable clamping device and coil-type spring.

Referring now to the drawings and particularly to FIGS. 1 and 2, there is shown an ankle and foot brace, generally designated by the numeral 50, which includes leg members 60, both having a first portion 65 of rod-like configuration and a second portion 70 of sleeve-like configuration. The first portion 65 has a smaller diameter than the second portion 70 which enables the first portion 65 to slide within the second portion 70. The overlapping relationship formed between the first and second portions 65 and 70, allows adjustment to the length of the leg members 60 to fit the wearer's leg. Other means for adjusting the leg members 60, although not illustrated, may be used in the present invention.

Respectively secured to the leg members 60 are two calf bands 75, respectively provided with mating patches 80 and 85 of synthetic materials which adhere when pressed together, such as those sold under the Trademark "Velcro". More particularly, the Velcro material includes a first patch providing a plurality of monofilament hooks and a second fabric pad which engages the hooks (not shown). Each of the calf bands 75 is of sufficient length to accommodate a wide range of circumferential adjustments in the length of the fastened-together patches, thereby to accommodate a wide range of calf sizes. The present invention contemplates the use of other means to attach the leg members 60 to the patient's calf. For example, and not intended as a limitation, straps, buckles, or laces could be utilized.

Each leg member 60 further includes a means for providing dorsiflexion assistance to the wearer's shoe 90. In the illustrated preferred embodiment, this assistance is provided by a spring 95 having a coil-like configuration which compresses as the shoe 90 is moved while walking. The resistance to compression assists in bringing the patient's shoe 90 to the standing upright position. By an appropriately forming the coil, the compression of the spring 95 may be changed to adjust the force which opposes and counterbalances the flexion to be assisted. The force exerted by the spring also can be adjusted by simply bending the leg members 60. Other types of springs or bias mechanisms are included in the present invention, the use of which primarily depends on the patients' needs.

Figure 3:
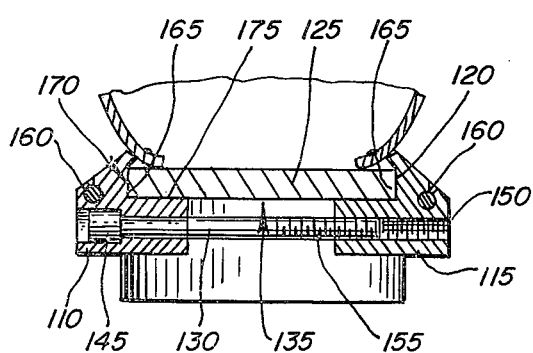
FIG. 3 is a cross-sectional view taken along Line 3—3 of FIG. 2, showing further details of the adjustable clamping device.

The lower ends 100 of leg members 60 are connected to a clamping device generally designated as 105. FIG. 3 provides a detailed illustration of the clamping device 105 which includes a first and second jaw designated as 110 and 115 respectively. The jaws 110, 115 each have a slot 120 for gripping the sole 125 of the shoe 90. A screw 130 traverses the sole 125 and parallels the underside 135 of the sole 125 to connect together the jaws 110, 115. The first jaw 110 includes a bore 140 which holds the head 145 of the screw 130. The second jaw 115 contains a bore 150 which is threaded to receive the threaded portion 155 of the screw 130. Rotating the head 145 of the screw 130 within the bore 140 to engage the threaded bore 150, tightens the clamping device 105 upon the sole 125 with positive gripping action. Thus, the ankle and foot brace 50 is connected to the shoe 90 without the need for drilling holes or otherwise damaging the shoe.

Each of the jaws 110, 115 contains a second bore 160 aligned parallel to the slot 120. The diameter of the second bore 60 is adapted to hold the leg members 60 with a snug fit. Further, each jaw 110, 115 preferably includes a first abutment surface 165 between the slot 120 and the edge 170 of the sole 125. A second abument surface 175 also is provided between the jaws 110, 115 and the underside 135 of the sole 125. These abutment surfaces 165, 175 provide additional stability to the clamping device 105 by distributing the force exerted through the clamping device 105 by the bias means over a larger area of the shoe 90. Thus, the clamping device is not twisted out of position and damage to the show is prevented.

Various clamping devices are intended for use with the present invention. Those devices which do not damage the wearer's shoe, such as the one illustrated herein, are preferred. The ability to adjust the clamping device for either the right or left foot of the patient is also preferred.

Figure 4:
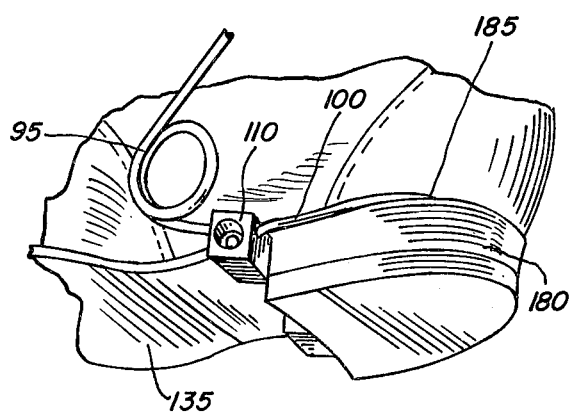
FIG. 4 is a fragmentary side perspective view of the ankle foot brace of FIG. 1, illustrating the coil-type spring which provides dorsiflexion assistance to the wearer's shoe.

Referring to FIG. 4, the lower ends 100 of the leg members extend through the second bores 160 rearward of the jaw 110 and toward the heel 180 of the shoe 90. The lower ends 100 make positive contact with the heel 180 at point 185 to prevent movement of the lower ends 100 of the leg members as force is exerted by the bias means to the shoe 90. The contact point 185 distributes the force to the heel 180 to assist the shoe 90 in returning to the standing upright position.

From the foregoing, it can be seen that there has been provided a novel ankle and foot brace usable on either leg of a patient and characterized by maximum adjustability to accommodate a wide variety of shoe and leg sizes. As demonstrated by these embodiments, this invention provides leg members which are longitudially and circumferentially adjustable, the circumferential adjustments including calf bands having Velcro fastening means thereon. Additionally, the ankle and foot braces may be attached to either the right or left shoe of a patient.

These embodiments also show that the present invention provides an ankle and foot brace which is easy and convenient to use due to the simplicity of attaching the brace to both the patient's shoe and leg. The ability to use the brace with a variety of conventional shoes having normal heels, without damaging the shoe by its attachment, will enhance the chances of providing a comfortable fit for the patient. The simplicity of design also adds to its relatively low cost of manufacture and the resultant affordability to the public.

While there has been described what is at present considered to be the preferred embodiments of the invention, it will be obvious to those skilled in the art that various changes in modifications may be made therein, without departing from the invention and that it is, therefore, the intent of the appended claims to cover all such changes and modifications as fall within the true spirit and scope of the invention.

What is claimed is:

1. An ankle and foot brace mountable to a shoe and adjustable readily to fit numerous sizes of shoes and legs, said brace comprising:

a pair of spaced leg members, each leg members having means for adjusting the length of said leg member;

adjustable means for attaching said brace to the calf of a wearer, said attachment means including a pair of calf bands respectively connected to opposite ends of said leg members, extending in use about said wearer's calf for respectively securing said leg members thereto, and cooperating to surround the wearer's calf, with the free ends of one of said calf bands respectively disposed and attachable in overlapping relationship with the free ends of the other said calf bands;

means for biasing the other end of each said leg member to provide dorsiflexion assistance to a wearer's shoe; and adjustable means for clamping said leg members adjacent to the lower ends thereof and attaching in use about said wearer's shoe for securing said leg members thereto, said clamping means carried by said leg members and extending rearward along and in contact with said wearer's shoe.

2. The ankle and foot brace set forth in claim 1, wherein said adjustable clamping means comprises a pair of jaws and an adjusting screw, each jaw having a slot for receiving the sole of the wearer's shoe, a first of said jaws having a bore for holding the head of said screw, a second of said jaws having a threaded bore for receiving the threaded portion of said screw, said screw traversing said sole and being parallel to the underside of said sole; each of said jaws having a second bore in parallel alignment to said slot for receiving said leg members and for abutting the lower ends of said leg members against the wearer's shoe, said lower ends extending through said second bore rearward of said jaw and toward the heel of the shoe.

3. An ankle and foot brace adjustable readily to fit numerous sizes of shoes and legs, said brace comprising:

a pair of spaced leg members having a rod-like configuration, each leg member having a first portion of rod-like configuration and a second portion of sleeve-like configuration to form an overlapping relationship, said first portion moving within said second portion to adjust the length of said leg members;

a pair of calf bands respectively connected to opposite sides of said leg members and cooperating to surround the wearer's calf with the free ends of one of said calf bands respectively disposed in overlapping relationship with the free ends of the other said calf band, and fastening means for securing together the overlapping ends of said calf bands;

a spring having a coil-like configuration, said spring being integrally formed with each of said leg members, each said spring being aligned to provide dorsiflexion assistance to the wearer's shoe; and an adjustable clamp having a pair of jaws and an adjustable screw, each jaw having a slot for receiving the sole of the wearer's shoe, said first jaw having a bore for holding the head of said screw, said second jaw having a threaded bore for receiving the threaded portion of said screw, said screw traversing the shoe's sole and being parallel to the underside of said sole, each of said jaws having a second bore in parallel alignment to said slot for receiving said leg members and for abutting the lower ends of said leg members against the heel of the wearer's shoe, said lower ends extending through said leg members against the heel of the wearer's shoe, said lower ends extending through said second bore rearward of said jaw and toward the heel of the shoe, each of said jaws having a first abutment surface for engaging the edge of said sole, and a second abutment surface for engaging the underside of said sole.

* * * * *